US00PP08289P

United States Patent [19]

Zary

[11] Patent Number: Plant 8,289

[45] Date of Patent: Jul. 6, 1993

[54] ROSE PLANT NAMED JACCOL

[75] Inventor: Keith W. Zary, Thousand Oaks, Calif.

[73] Assignee: Bear Creek Gardens, Inc., Medford, Oreg.

[21] Appl. No.: 795,670

[22] Filed: Nov. 21, 1991

[51] Int. Cl.[5] ..... A01H 5/00

[52] U.S. Cl. ..... Plt./18

[58] Field of Search ..... Plt. 18–20

*Primary Examiner*—Howard J. Locker

*Attorney, Agent, or Firm*—Klarquist, Sparkman, Campbell, Leigh & Whinston

[57] ABSTRACT

A hybrid tea class rose variety having long stems averaging 24 inches long, high cut-flower production, good vase life of cut blooms averaging 8 days from cutting stage, very strong stems, large attractive flower, very upright growth habit, making it easy to manage as a cut-flower crop.

1 Drawing Sheet

1

The present invention relates to a new and distinct variety of rose plant of the hybrid tea class which was originated by me by crossing the variety KORenlo, U.S. Plant Pat. No. 5,679, with an unnamed breeding line.

The primary objective of this breeding was to produce a new rose variety having the high greenhouse cut flower production of KORenlo, its excellent vase life, and its upright habit of growth, combined with the larger flower, fragrance, and long stems of the red hybrid tea breeding line. The objective was substantially achieved along with other desirable improvements as evidenced by the following unique combination of characteristics which are outstanding in the new variety and which distinguish it from its parents, as well as from all other varieties of which I am aware:

1. Long stems, averaging 24 inches.
2. High cut-flower production.
3. Good vase life, averaging 8 days from cutting stage.
4. Very strong stems.
5. Large attractive flowers.
6. Very upright growth habit, making it easy to manage as a cut-flower crop.

Asexual reproduction of this new variety by budding, as performed at Somis, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color terminology in accordance with The Royal Horticultural Society (London) Colour Chart, except where ordinary dictionary significance of color is indicated.

Parentage:

*Seed parent.*—KORenlo, U.S. Plant Pat. No. 5,679.

*Pollen parent.*—An unnamed breeding line.

Classification:

*Botanical.*—*Rosa hybrida.*

*Commercial.*—Hybrid tea.

2

FLOWER

Observations made from specimens grown in a greenhouse environment in Somis, Calif., from January to February, 1990.

Blooming habit: Recurrent.

Bud:

*Size.*—About 1½ inches long when the petals start to unfurl.

*Form.*—The bud form is long, pointed ovoid.

*Color.*—When sepals first divide, bud color is Red Group 50C. When half blown, the upper and lower sides of the petals are Red Group 55C.

*Sepals.*—Color: Green Group 137C, with a pronounced lighter streak down the center of each sepal. Surface texture: Covered with fine hairs. There are two normally appendaged sepals and one heavily appendaged sepal. There are two unappendaged sepals with hairy edges.

*Receptacle.*—Color: Green Group 137D. Shape: Funnel. Size: Large, about ½ inch × ½ inch. Surface: Smooth.

*Peduncle.*—Length: Long, averaging about 4½ to 5 inches. Surface: Smooth, with an occasional very fine prickle. Color: Medium green. Strength: Stiff, erect.

Bloom:

*Size.*—Large. Average open diameter is 5 inches.

*Borne.*—Singly.

*Stems.*—Long, strong, average length is about 24 inches.

*Form.*—When first open, bloom has high center. Permanence of bloom retains its form to the end, and outer petals curl back with slight quilling.

*Petalage.*—Number of petals under normal conditions: 30.

*Color.*—The upper and reverse sides of the petals are Red Group 55C. The base of petals has a small yellowish half-moon at the point of attachment. The major color on the upper side is Red Group 55C.

*Variegations.*—None.

*Discoloration.*—No general tonality at the end of the first day and at the end of the third day.

*Fragrance.*—Slight.

Petals:

*Texture.*—Thick, leathery.

*Shape.*—Round to deltoid.

*Form.*—Tips slightly recurved, edges slightly quilled.

*Arrangement.*—Imbricated, the few, small petaloids in the center.

*Persistence.*—Petals drop off cleanly before drying.

*Lastingness.*—On the plant: Long, about 5 to 7 days. As a cut flower: Long, about 7 to 9 days.

Reproductive parts:

*Anthers.*—Size: Large. Quantity: Many. Color: Yellow. Arrangement: Regular around styles.

*Filaments.*—Color: Reddish brown.

*Pollen.*—Color: Lemon yellow.

*Styles.*—Color: Reddish.

*Stigmas.*—Color: Greenish white.

Plant:

*Form.*—Bush.

*Growth.*—Very vigorous, upright, branching.

Foliage:

*Number of leaflets on normal mid-stem leaves.*—5.

*Size.*—Large, about 6½ inches long.

*Quantity.*—Normal.

*Color.*—New foliage: Bronze green. Old foliage: Dark green.

Leaflets:

*Shape.*—Pointed oval.

*Texture.*—Upper side: Leathery, glossy.

*Edge.*—Serrated.

*Serration.*—Single, small.

*Petiole rachis.*—Color: Green.

*Petiole underside.*—Smooth, with an occasional prickle.

*Stipules.*—Medium, about ½ inch long, bearded.

*Disease resistance.*—Susceptible to mildew under normal growing conditions at Somis, Calif. As this is a greenhouse rose and not grown outdoors, it has not been tested for blackspot or rust.

Wood:

*New wood.*—Color: Reddish. Bark: Smooth.

*Old wood.*—Color: Green. Bark: Smooth.

Prickles:

*Quantity.*—Ordinary quantity on main canes from base and on laterals from main canes.

*Form.*—Medium, about ¼ inch, hooked slightly downward.

*Color when young.*—Red.

Small prickles:

*Quantity.*—None on main stalks or on laterals.

Other traits, characteristics or markings: The variety was bred as a greenhouse cut flower variety. Under Somis, Calif., conditions, it produces 28 stems per plant per year or 190–200 stems per square meter of greenhouse. This makes it high yielding for a hybrid tea. The standard varieties would yield 22–25 stems per plant per year in Somis, Calif.

I claim:

1. A new and distinct variety of rose plant of the hybrid tea class, substantially as herein shown and described, characterized particularly as to novelty by the unique combination of its high cut-flower production, upright habit of growth, long, strong stems, good vase life of cut blooms, and large, attractive flowers.

* * * * *

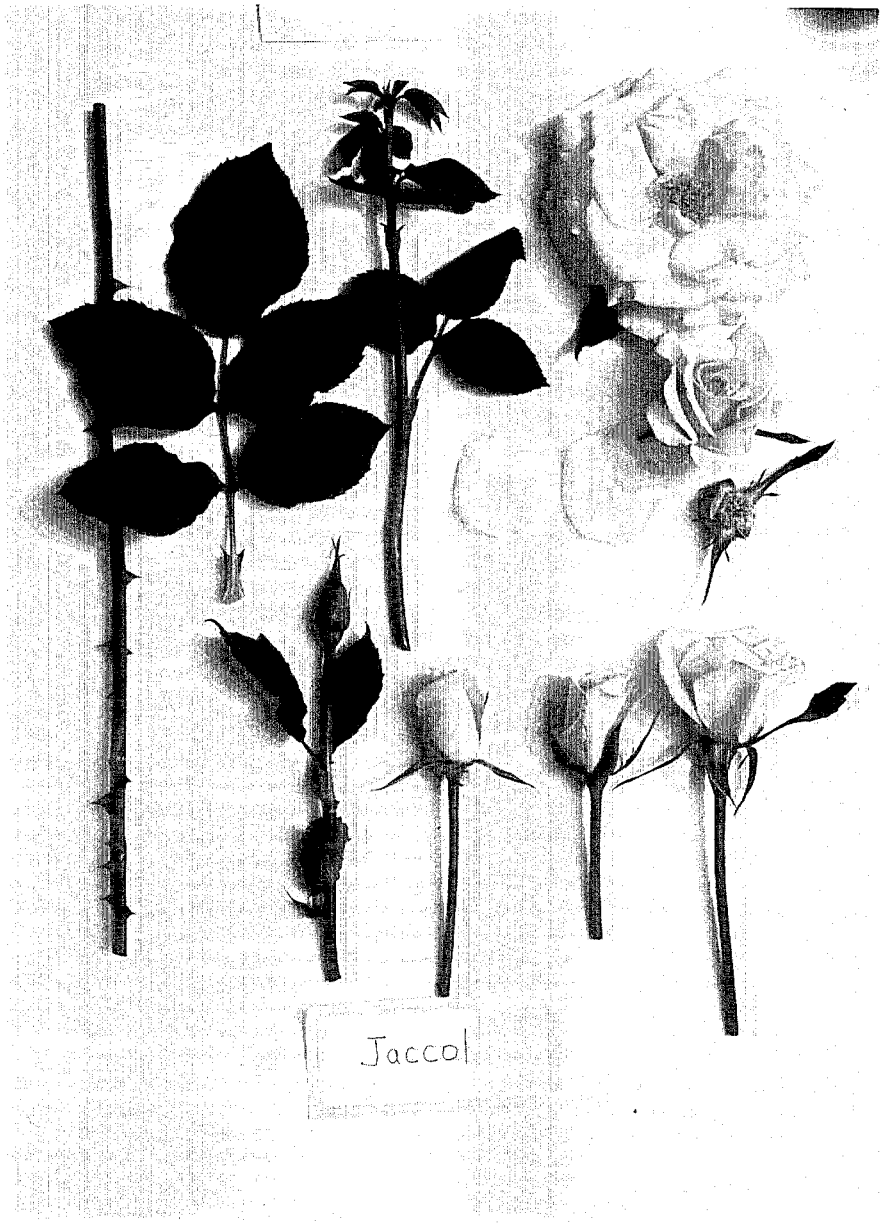
Jaccol